United States Patent
Buettner

(10) Patent No.: US 9,702,792 B2
(45) Date of Patent: Jul. 11, 2017

(54) TRANSPORT DEVICE FOR SAMPLES IN A MICROTOME

(71) Applicant: Leica Biosystems Nussloch GmbH, Nussloch (DE)

(72) Inventor: René Buettner, Mannheim (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 427 days.

(21) Appl. No.: 14/324,288

(22) Filed: Jul. 7, 2014

(65) Prior Publication Data

US 2015/0023768 A1 Jan. 22, 2015

(30) Foreign Application Priority Data

Jul. 16, 2013 (DE) .................. 10 2013 213 955
Sep. 24, 2013 (DE) .................. 10 2013 219 171

(51) Int. Cl.
*G01N 1/06* (2006.01)
*G01N 35/04* (2006.01)

(52) U.S. Cl.
CPC ............... *G01N 1/06* (2013.01); *G01N 35/04* (2013.01); *G01N 2001/065* (2013.01)

(58) Field of Classification Search
None
See application file for complete search history.

(56) References Cited

U.S. PATENT DOCUMENTS

| 2005/0235542 A1 | 10/2005 | Metzner et al. |
| 2008/0113440 A1 | 5/2008 | Gurney et al. |
| 2009/0065709 A1 | 3/2009 | Fischer et al. |
| 2009/0146335 A1 | 6/2009 | Schmitt |
| 2010/0030364 A1 | 2/2010 | Fujimoto et al. |
| 2010/0058913 A1 | 3/2010 | Walter |

FOREIGN PATENT DOCUMENTS

GB 2463133 3/2010

*Primary Examiner* — Robert R Raevis
(74) *Attorney, Agent, or Firm* — Hodgson Russ LLP

(57) ABSTRACT

A transport device (100) for samples (310) in a microtome having a transport arm (112) that is mounted longitudinally movably, has an entraining element (114) mounted pivotably on the transport arm. The entraining element is movable into a first position in which it entrains a sample present on a transport path, and into a second position in which it does not entrain a sample present on the transport path. The transport device has a positioning mechanism for the entraining element having a positioning element and a gate (130) with two tracks (131, 132) extending alongside one another for the positioning element. The entraining element is obligatorily located in the first position when the positioning element is moved in a first (131) of the two tracks, and the entraining element is obligatorily located in the second position when the positioning element is moved in a second (132) of the two tracks.

7 Claims, 3 Drawing Sheets

TRANSPORT DEVICE FOR SAMPLES IN A MICROTOME

CROSS REFERENCE TO RELATED APPLICATIONS

This application claims priority of German patent application number 10 2013 213 955.1 filed Jul. 16, 2013, and of German patent application number 10 2013 219 171.5 filed Sep. 24, 2013. The entire disclosure of both priority applications is incorporated by reference herein.

FIELD OF THE INVENTION

The present invention relates to a transport device for samples in a microtome.

BACKGROUND OF THE INVENTION

A transport device for samples (usually a cassette having tissue embedded in paraffin) in a microtome proceeds from DE 10 2008 046 395 A1. The transport device serves to transport a sample out of a storage apparatus into a sample holder where the sample can be processed, in this case in particular sectioned. The transport device comprises for this purpose a drive apparatus and a pusher mechanism, coupled to the drive apparatus, that pushes a sample out of the storage apparatus into the sample holder. If a sample is meanwhile already located in the sample holder, it is thereby pushed out of the sample holder on the side located oppositely to the storage apparatus. There it must be picked up manually, which presents an appreciable risk of injury due to the proximity of the microtome knife. Alternatively, a further storage apparatus must be arranged there; this requires considerable installation space and makes the entire configuration relatively complex.

EP 2 301 665 A1 presents a specimen slide transport mechanism for a laser scanner device, in which a specimen slide can be moved back and forth between a storage location and a sample stage by means of a pusher having a pivotable flap. In particular, the flap can be tilted around an axis in order to entrain a specimen slide or to be moved along over it.

It is desirable to have available a transport device for samples which also permits, in a simple but robust manner, return transport out of the sample holder into the storage apparatus. As a result, the necessary installation space on the side of the sample holder located oppositely to the storage apparatus is reduced, and already-processed samples are automatically introduced back into the storage apparatus, thereby precluding a risk of injury due to the microtome knife.

SUMMARY AND ADVANTAGES OF THE INVENTION

The present invention proposes a transport device for samples in a microtome. A transport device according to the present invention offers a simple, reliable, and automated capability for moving samples back and forth in a microtome. An entraining element entraining the sample, on a transport arm movable in one direction back and forth, can be brought for that purpose into two different positions, namely a first position in which it entrains a sample present on a transport path, and into a second position in which it does not entrain a sample present on the transport path. The transport device is embodied so that the entraining element can be brought into the first or into the second position as a function of a motion sequence of the transport arm.

It is thereby possible for the entraining element to entrain a sample when said element is in the first position, and for the entraining element to be moved along over a sample when said element is in the second position.

A positioning mechanism for the entraining element comprises two tracks, e.g. in the form of a gate or slideways, extending next to one another, for a positioning element of the entraining element; the entraining element is obligatorily or automatically located in the first position when the positioning element is moved in a first of the two tracks, and the entraining element is obligatorily present in the second position when the positioning element is moved in a second of the two tracks. A positive guidance system of this kind is particularly robust and dependable because the position of the entraining element then does not depend on motors, springs, and the like which, if applicable, can also be defective.

A change in position is usefully effected automatically each time the positioning element reaches specific reversing points in at least one switching region at the end of the respective track. This is preferably achieved by the fact that the switching region comprises at least one one-way switch which is embodied so that upon passage in the one direction it directs the positioning element from one track into the other track, and upon passage in the other direction it does not direct the positioning element from the one track into the other track. It is thereby possible to bring the entraining element in controlled fashion into the respective other of the two positions with no need for a separate drive for that purpose. Instead, the drive system for moving the transport arm is sufficient also for bringing the entraining element into the other position, by the fact that the motion of the transport arm is simply reversed at the relevant reversing point.

Each switching region preferably comprises two contra-directionally operating one-way switches, so that a track change in both directions is possible. Two reversing points, each of which is associated with exactly one of the two tracks, then consequently exist in each switching region. When a first of the reversing points is traveled to, this causes the positioning element to take the first track after the reversal of the motion direction. When a second of the reversing points is traveled to, this causes the positioning element to take the second track after the reversal of the motion direction. A controlled track change occurs by the fact that either the first or the second reversing point is traveled to. The entraining element can thus be brought into the first or into the second position as a function of a motion sequence of the transport arm. It is thereby possible to bring the entraining element in controlled fashion into a desired one of the two positions in each switching region.

The invention thereby creates the capability of both moving the transport arm translationally back and forth, and switching the entraining element between the positions, by means of a single drive system (preferably a stepping motor) that causes a translational motion of the transport arm.

Further advantages and embodiments of the invention are evident from the description and the appended drawings.

It is understood that the features recited above and those yet to be explained below are usable not only in the respective combination indicated, but also in other combinations or in isolation, without departing from the scope of the present invention.

BRIEF DESCRIPTION OF THE DRAWING VIEWS

The invention is schematically depicted in the drawings on the basis of an exemplifying embodiment, and will be described in detail below with reference to the drawings.

DETAILED DESCRIPTION OF THE INVENTION

Figure 1:
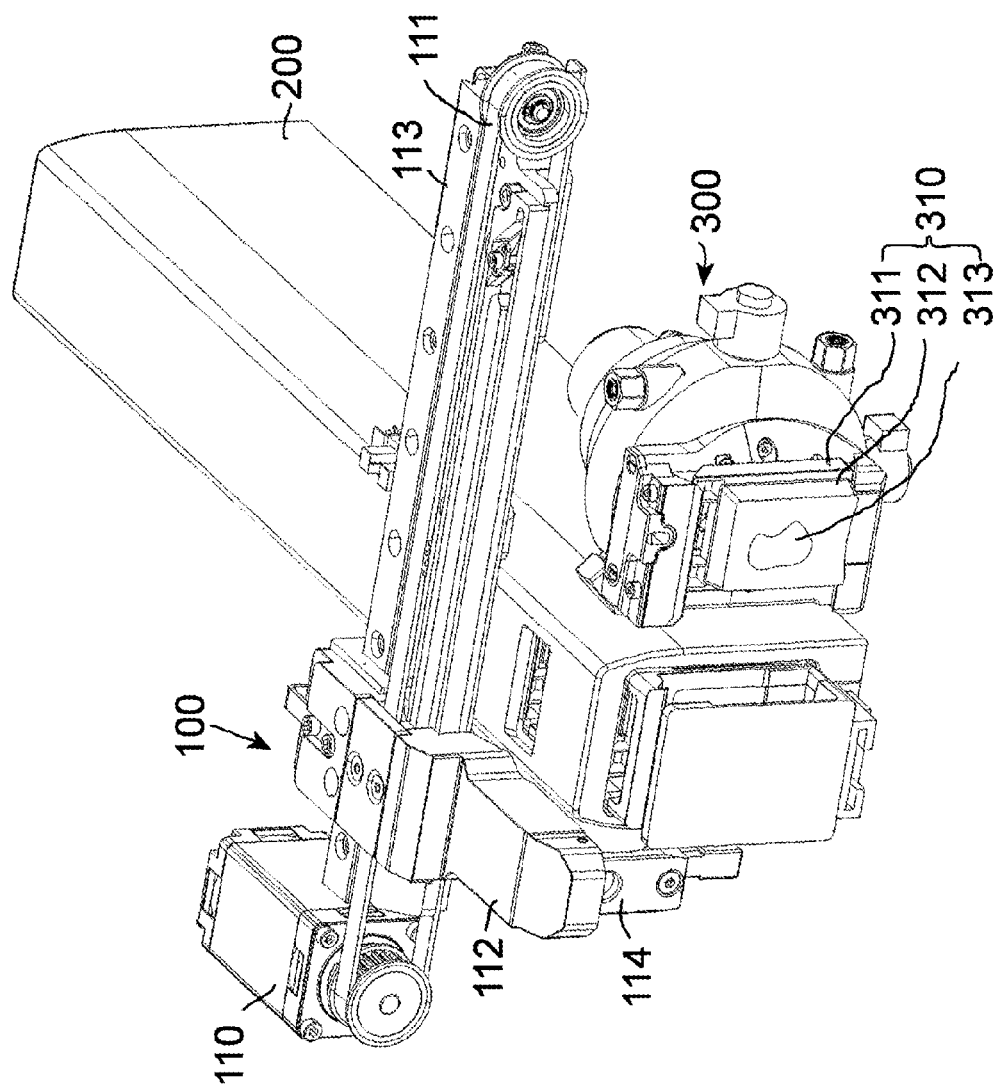
FIG. 1 is a perspective depiction of a contour view of a preferred embodiment of a transport device according to the present invention, together with a storage apparatus and a sample holder having a sample received therein.
Figure 2:
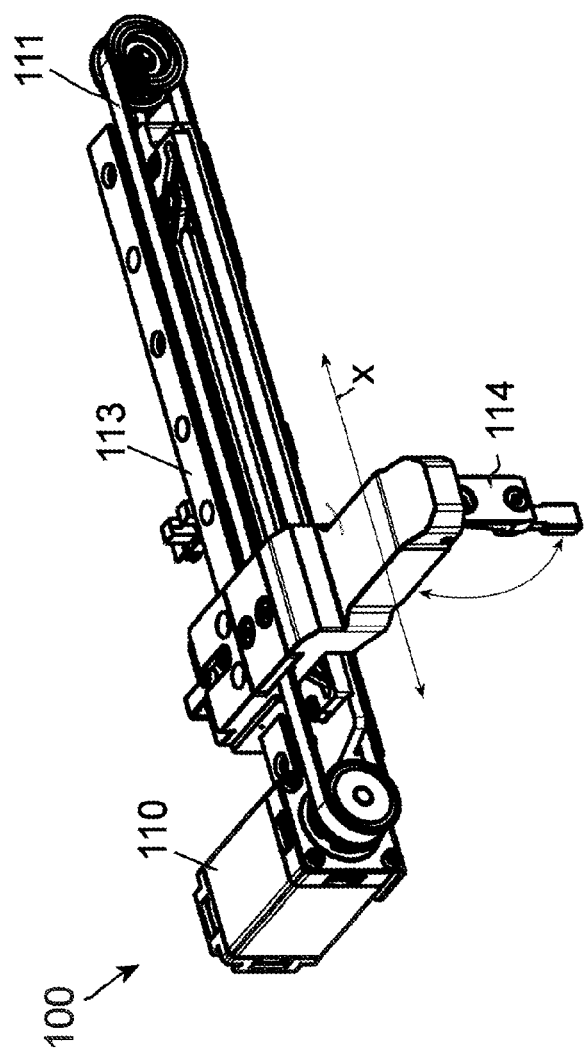
FIG. 2 depicts, for better illustration, only the transport device of FIG. 1.
Figure 3:
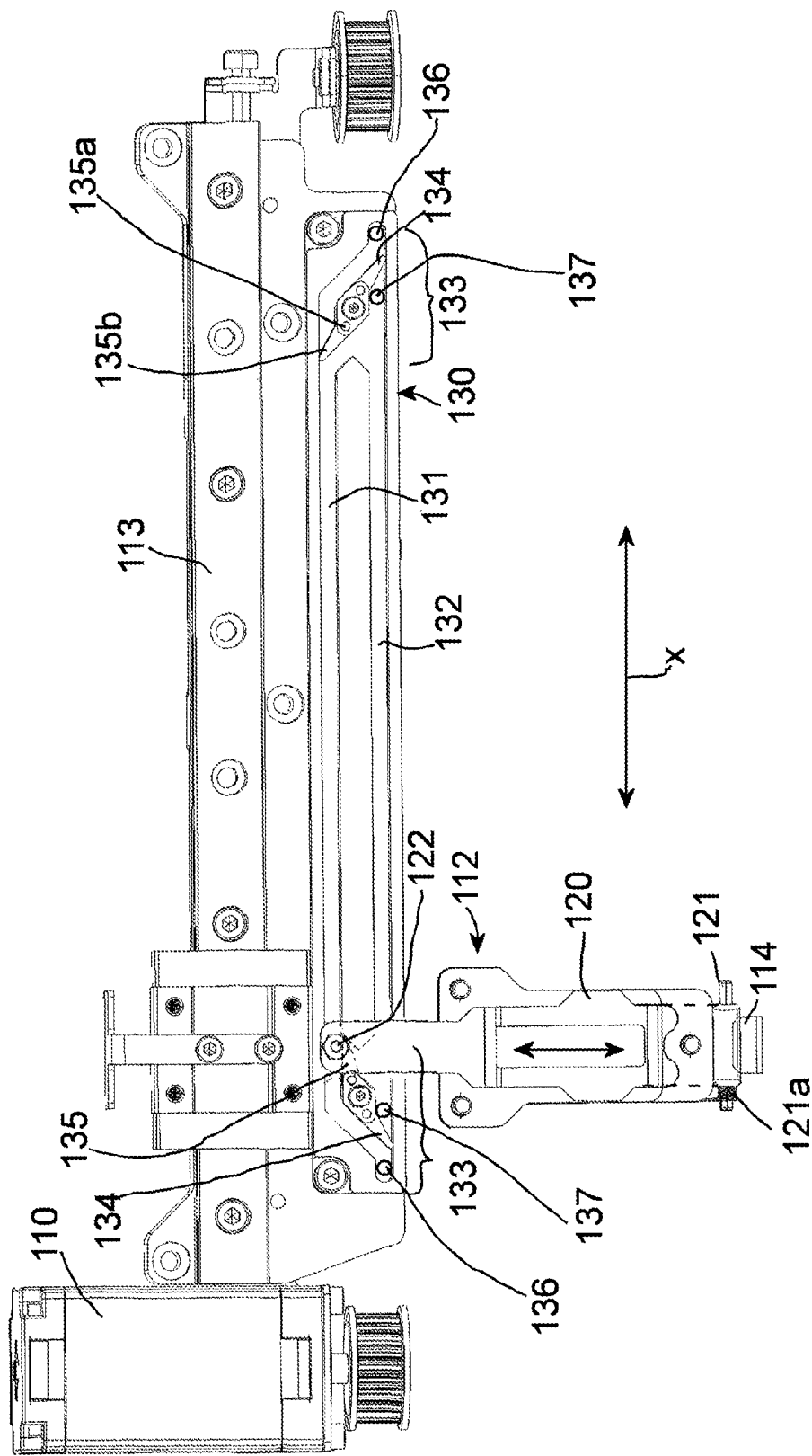
FIG. 3 shows, from above, a portion of the transport device of FIG. 1.

FIGS. 1 to 3 are described interconnectedly and in overlapping fashion, identical elements being labeled with identical reference characters. Be it noted that for better illustration, not all components are always shown in the Figures.

FIG. 1 is a perspective view of a preferred embodiment of a transport device 100 according to the present invention together with a storage apparatus 200 and a sample holder 300 of a microtome. A sample 310, which is made up of a cassette 311 and tissue 313 held thereby and embedded in paraffin 312, is held in the sample holder. FIG. 1 serves to provide an overview of the existing components of the microtome. A knife (not depicted) is arranged below sample holder 300 and serves to cut off thin slices of paraffin 312 having tissue 313.

Transport device 100 is provided above the motion region. The risk of contamination is thus lower, and the compact system is able to keep the working area clear during sectioning. Parallel operations are also possible here. A further advantage of the arrangement is the modular design. While a system that is located beneath the motion region possibly results in additional outlay for assembly, for example in the context of refitting of the module, the solution depicted here can readily be assembled and disassembled from above, even (depending on the design) with no need to disassemble the housing.

Transport device 100 itself is depicted in FIG. 2, and serves to transport samples 310 out of storage apparatus 200 into sample holder 300 and vice versa. It comprises for that purpose an electrical drive system 110 that is embodied here as a stepping motor. Stepping motor 110 drives a belt 111 that is fixedly connected to a transport arm 112 that is mounted movably in a direction X along a rail 113. Arranged on transport arm 112 is a swingable entraining element 114 that, in the first position depicted in FIGS. 1 and 2, entrains sample 310 in the context of a motion in the X direction, and in a swung-in second position (not depicted) does not entrain a sample 310 in the context of a motion in the X direction but instead travels past above it.

Transport apparatus 100 is embodied so that a change in position, i.e. a changeover of the entraining element from the first into the second position and vice versa, is effected automatically by the fact that transport arm 112 travels to specific reversing points in switching regions. This is depicted in more detail in FIG. 3.

As mentioned, entraining element 114 is mounted pivotably on transport arm 112, the pivoting being brought about by linear displacement of a displacement plate 120. For that purpose, entraining element 114 is mounted rotatably on a rotation axis 121 of transport arm 112. Entraining element 114 is preloaded by means of a spring 121a into the first (swung-out) position. In this position, a sample is entrained by a lower part of the entraining element below rotation axis 121.

Displacement plate 120 is mounted on transport arm 112 linearly displaceably in the drawing plane, as indicated by the double arrow, and can press against an upper part of the entraining element above rotation axis 121. As displacement plate 120 continues to be displaced toward entraining element 114, it ultimately presses against the upper part of the entraining element, which results in a pivoting of entraining element 114 against the spring force of spring 121a around rotation axis 121, and thus causes an inward swing. When displacement plate 120 is displaced back toward rail 113, spring 121a swings entraining element 114 back out into the first position.

When displacement plate 120 is in the position shown in FIG. 3 (displaced toward rail 113), entraining element 114 is therefore also in the (swung-out) first position. When plate 120 in FIG. 3 is displaced toward entraining element 114, however, this causes entraining element 114 to swing in or swing over into the second (swung-in) position.

The displacement of displacement plate 120 is accomplished via a peg 122 that can run in a first track 131 or a second track 132 of a gate 130. Gate 130 comprises two switching regions 133 at its two ends, which are used for changing the track of peg 122 between tracks 131 and 132. Gate 130, peg 122 (which is guided as a sliding block), and displacement plate 120 are constituents of a positioning mechanism for the entraining element.

Each switching region possesses two one-way switches 134, 135 that respectively permit peg 122 to pass in one direction, but in the other direction force the peg to change tracks. A one-way switch 135 here has a spring-loaded tab 135b that is mounted pivotably on a rotation point 135a and is preloaded against an outer wall of the gate. All that is possible, from this rest position, is a motion of the tab away from the outer wall in order to allow the peg to pass between the rotation point and outer wall.

Referring to switching region 133 depicted on the right in FIG. 3, the result of this is that two reversing points 136, 137 exist; first reversing point 136 causes peg 122 to be located in first track 131 upon a motion from 136 to the left in FIG. 3, whereas second reversing point 137 causes peg 122 to be located in second track 132 upon a motion from 137 to the left in FIG. 3. Corresponding reversing points are also located in left switching region 133. There as well, reversing point 136 is associated with first track 131, and reversing point 137 with second track 132.

With reference to FIG. 3, in order to transfer a sample out of storage apparatus 200 into sample holder 300, transport arm 112 is firstly moved to the left to reversing point 136 (i.e. peg 122 is located at the reversing point). Upon return travel to the right, peg 122 is thereby forced into track 131, so that entraining element 114 swings out and entrains a sample out of storage apparatus 200 into sample holder 300. Once the sample has arrived in the sample holder, the motion of transport arm 112 is stopped. It can then usefully be moved back to the left in order not to impede processing of the sample. A magazine (like that of a slide projector) in storage apparatus 200 is so far usefully unmodified, in order not to prevent the entraining element from traveling through the now-open magazine space. Alternatively, the magazine can also be moved back out of the travel path of the entraining element (to the rear in FIG. 1).

If a processed sample is to be transferred back out of sample holder 300 into storage apparatus 200, transport arm 112 is firstly moved to the left to reversing point 137 (i.e. peg 122 is located at the reversing point). Upon travel to the left, reversing point 137 is in any event reached before reversing point 136, since the upper one-way switch 135 directs the peg, if it is located in track 131, into track 132. Entraining element 114 is thereby swung in.

Upon subsequent movement to the right, peg 122 thereby remains in track 132, so that entraining element 114 remains swung in and can be moved along over the sample in sample holder 300. Transport arm 112 is then moved to the right to reversing point 136. Upon return travel to the left, peg 122 is thereby forced into track 131 so that entraining element 114 swings out and entrains a sample out of sample holder 300 into storage apparatus 200. Once the sample has arrived in storage apparatus 200, the motion of transport arm 112 is stopped.

In order to allow continued motion farther to the left without sample entrainment by storage apparatus 200, the magazine can be moved back out of the travel path of the entraining element, or transport arm 112 can be moved back to the right to reversing point 137 so that the entraining element swings in, whereupon transport arm 112 is moved again to the left.

Another sample can then be placed in the travel path of the entraining element, for example by corresponding position of the magazine, so that said sample can then be transferred into the sample holder.

The above-described configuration permits a translational motion of transport arm 112 and thus of entraining element 114 in an X direction, and simultaneously a swinging in and out of entraining element 114, to be enabled by means of a single drive system 110, so that entraining element 114 in the swung-in state can be moved past a sample present in sample carrier 300 in order then, after swinging out, to introduce it back into the storage apparatus in particular in the context of the return motion.

What is claimed is:

1. A transport device for samples in a microtome, the transport device comprising:
    a transport arm;
    an entraining element (114) pivotably mounted on the transport arm (112), the entraining element having a first position wherein the entraining element (114) entrains a sample (310) present on a transport path and a second position wherein the entraining element (114) does not entrain a sample present on the transport path; and
    a positioning mechanism for the entraining element, the positioning mechanism including a positioning element and a gate (130) having two tracks (131, 132) extending next to one another for receiving the positioning element, the entraining element being located in the first position when the positioning element is moved in a first (131) of the two tracks, and the entraining element being located in the second position when the positioning element is moved in a second (132) of the two tracks, wherein the gate (130) has at least one switching region (133) where the two tracks (131, 132) are brought together.

2. The transport device (100) according to claim 1, wherein the positioning element includes a peg (122) for receipt by the two tracks (131, 132), and the positioning mechanism includes a displacement plate (120) coupling the peg (122) to the entraining element (114).

3. The transport device (100) according to claim 1, wherein the gate (130) includes at least one one-way switch (134, 135) provided in the at least one switching region (133) and configured so that upon passage of the positioning element in one direction the one-way switch directs the positioning element from one of the two tracks to the other of the two tracks, and upon passage of the positioning element in another direction the one-way switch does not direct the positioning element from one of the two tracks to the other of the two tracks.

4. The transport device (100) according to claim 3, wherein the at least one one-way switch (134, 135) has a spring-loaded tab (135b) mounted pivotably at a rotation point (135a).

5. The transport device (100) according to claim 3, wherein the at least one one-way switch comprises two contradirectionally passable one-way switches (134, 135).

6. The transport device (100) according to claim 1, wherein the at least one switching region (133) includes a first reversing point (136), the positioning element being moved, starting from the first reversing point (136), into the first (131) of the two tracks when the motion direction of the positioning element is reversed at the first reversing point (136).

7. The transport device (100) according to claim 6, wherein the at least one switching region (133) includes a second reversing point (137), the positioning element being moved, starting from the second reversing point (137), into the second (132) of the two tracks when the motion direction of the positioning element is reversed at the second reversing point (137).

* * * * *